United States Patent
Hong et al.

(10) Patent No.: US 9,850,326 B2
(45) Date of Patent: Dec. 26, 2017

(54) LIGAND COMPOUND, METALLOCENE COMPOUND, AND METHOD FOR PREPARATION OF OLEFIN-BASED POLYMER USING THE SAME

(71) Applicant: LG CHEM, LTD., Seoul (KR)

(72) Inventors: Bog Ki Hong, Daejeon (KR); Yong Ho Lee, Daejeon (KR); Chang Woan Han, Daejeon (KR); Yi Young Choi, Daejeon (KR); Ki Soo Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/026,119

(22) PCT Filed: Aug. 21, 2015

(86) PCT No.: PCT/KR2015/008771
§ 371 (c)(1),
(2) Date: Mar. 30, 2016

(87) PCT Pub. No.: WO2016/056744
PCT Pub. Date: Apr. 14, 2016

(65) Prior Publication Data
US 2016/0319050 A1 Nov. 3, 2016

(30) Foreign Application Priority Data

Oct. 6, 2014 (KR) ........................ 10-2014-0134342
Aug. 20, 2015 (KR) ........................ 10-2015-0117300

(51) Int. Cl.
| | |
|---|---|
| *C07F 17/00* | (2006.01) |
| *C08F 4/6592* | (2006.01) |
| *C08F 10/00* | (2006.01) |
| *C08F 10/02* | (2006.01) |
| *C08F 210/16* | (2006.01) |
| *C07F 7/08* | (2006.01) |
| *C08F 4/659* | (2006.01) |

(52) U.S. Cl.
CPC ............ *C08F 10/02* (2013.01); *C07F 7/0812* (2013.01); *C07F 17/00* (2013.01); *C08F 4/65927* (2013.01); *C08F 210/16* (2013.01); *C08F 4/65908* (2013.01); *C08F 4/65912* (2013.01); *C08F 4/65916* (2013.01); *C08F 10/00* (2013.01); *C08F 2420/06* (2013.01)

(58) Field of Classification Search
CPC .. C07F 17/00; C08F 4/65927; C08F 4/65908; C08F 4/6592; C08F 10/00
See application file for complete search history.

(56) References Cited

U.S. PATENT DOCUMENTS

| | | | |
|---|---|---|---|
| 5,064,802 | A | 11/1991 | Stevens et al. |
| 6,683,150 | B1 | 1/2004 | Meverden et al. |
| 2002/0193535 | A1 | 12/2002 | Meverden et al. |
| 2003/0148877 | A1 | 8/2003 | Nifant'ev et al. |
| 2003/0195306 | A1 | 10/2003 | Tsuie et al. |
| 2003/0229188 | A1 | 12/2003 | Nagy et al. |
| 2005/0228156 | A1 | 10/2005 | Holland et al. |
| 2008/0076891 | A1 | 3/2008 | Wang et al. |
| 2013/0296497 | A1 | 11/2013 | Jeong et al. |

FOREIGN PATENT DOCUMENTS

| | | |
|---|---|---|
| CN | 1646583 A | 7/2005 |
| CN | 1934148 A | 3/2007 |
| CN | 103339162 A | 10/2013 |
| EP | 3012261 A1 | 4/2016 |
| KR | 2000-0069979 A | 11/2000 |
| KR | 10-2012-0087706 A | 8/2012 |
| KR | 10-2015-0015789 A | 2/2015 |
| KR | 10-2015-0057964 A | 5/2015 |
| KR | 10-2015-0065084 A | 6/2015 |

OTHER PUBLICATIONS

I.E. Nifant'ev et al.: "Synthesis and study of the mutagenic activity of di(indeno[2,1-b]indolyl)- and di(indeno[2,1-b]pyrrolyl)methanes and -dimethylsilanes", Russian Chemical Bulletin, International Edition, vol. 50, No. 8, pp. 1439-1445, Aug. 2001.
Database WPI Week 201543, Thomson Scientific, May 2015, 6 pages, XP002767349.

*Primary Examiner* — Caixia Lu
(74) *Attorney, Agent, or Firm* — Dentons US LLP

(57) ABSTRACT

The present invention relates to a novel ligand compound, a metallocene compound, and a method for preparing an olefin-based polymer using the same. The metallocene compound according to the present invention and a catalyst composition comprising the same have excellent polymerization activity, and yet, have excellent comonomer insertion capability, and thus, can be used to prepare olefin-based polymer having wide molecular weight distribution and the resulting excellent processability.

8 Claims, No Drawings

LIGAND COMPOUND, METALLOCENE COMPOUND, AND METHOD FOR PREPARATION OF OLEFIN-BASED POLYMER USING THE SAME

CROSS REFERENCE TO RELATED APPLICATIONS

This application is a National Stage Entry of International Application No. PCT/KR2015/008771, filed on Aug. 21, 2015, and claims the benefit of and priority to Korean Application No. 10-2014-0134342, filed on Oct. 6, 2014 and Korean Application No. 10-2015-0117300, filed on Aug. 20, 2015, all of which are incorporated herein by reference in their entirety for all purposes as if fully set forth herein.

TECHNICAL FIELD

The present invention relates to a novel ligand compound, a metallocene compound, and a method for preparing an olefin-based polymer using the same.

BACKGROUND OF ART

Dow Company presented [Me2Si(Me4C5)NtBu]TiCl2 (Constrained-Geometry Catalyst, hereinafter abbreviated as CGC) in the early 1990's (U.S. Pat. No. 5,064,802), and the advantages of CGC in the copolymerization reaction of ethylene and alpha-olefin, compared to the previously known metallocene catalysts, can be summarized as follows: (1) it exhibits high activity even at high polymerization temperature, and yet, produces a high molecular weight polymer, and (2) it also has very excellent copolymerizability with alpha-olefins having large steric hindrance such as 1-hexene and 1-octene. In addition, as various properties of CGC in a polymerization reaction have been gradually known, there have been vigorous attempts to synthesize derivatives thereof and use as polymerization catalysts in academic and industrial fields.

A Group 4 metallocene compound having one or two cyclopentadienyl groups as ligand may be activated with methylaluminoxane or a boron compound to be used as a catalyst of olefin polymerization. Such catalyst exhibits unique properties that cannot be realized by a Ziegler-Natta catalyst of the prior art.

Specifically, a polymer obtained using the catalyst has narrow molecular weight distribution and better reactivity to second monomers such as alpha-olefin or cyclic olefin, and the distribution of the second monomers of the polymer is uniform. Also, by changing substituents of the cyclopentadienyl ligand in the metallocene catalyst, stereoselectivity of the polymer may be controlled when polymerizing alpha olefin, and a degree of copolymerization, a molecular weight, and the distribution of second monomers and the like may be easily controlled, when copolymerizing ethylene with other olefins.

Meanwhile, since a metallocene catalyst is expensive compared to the Ziegler-Natta catalyst of the prior art, it should have good activity so as to have economical value. If reactivity to second monomers is good, a polymer including many second monomers may be obtained even with a small amount of second monomers introduced.

Many researchers have studied on various catalysts, and as a result, it was proved that bridged catalysts generally have good reactivity to second monomers. Bridged catalysts studied till now can be classified into three kinds according to the shapes of bridges. The first is a catalyst wherein two cyclopentadienyl ligands are connected by an alkylene dibridge by the reaction of electrophile such as alkyl halide with indene or fluorene and the like, the second is a silicon-bridged catalyst connected by —SiR2-, and the third is a catalyst a methylene-bridged catalyst obtained from the reaction of fulvene with indene or fluorene and the like.

However, among these attempts, a few catalysts are practically applied in commercial plants, and there has been continued demand for the preparation of catalysts exhibiting more improved polymerization performance.

DETAILED DESCRIPTION OF THE INVENTION

Technical Problem

In order to overcome the above problems of the prior art, it is an object of the invention to provide a metallocene compound that has excellent polymerization activity, and yet, has excellent comonomer insertion capability, and thus, can be used to prepare an olefin-based polymer having wide molecular weight distribution and the resulting excellent processability, and a method for preparing an olefin-based polymer using the same.

Technical Solution

In order to achieve the object, one aspect of the invention provides a ligand compound represented by the following Chemical Formula 1:

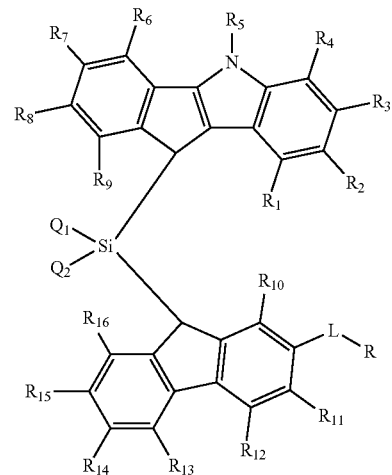

[Chemical Formula 1]

in the Chemical Formula 1, $R_1$ to $R_{16}$ are identical or different, and are independently, hydrogen, halogen, a C1-20 alkyl group, a C2-20 alkenyl group, a C3-20 cycloalkyl group, a C4-20 cycloalkylalkyl group, a C1-20 alkoxy group, a C6-20 aryl group, a C5-20 heteroaryl group, a C7-20 alkylaryl group, or a C7-20 arylalkyl group, and two or more neighboring groups of $R_1$ to $R_{16}$ may be connected with each other to form a substituted or unsubstituted aliphatic or aromatic ring, provided that all of $R_1$ to $R_{16}$ are not hydrogen;

L is a direct bond or a C1-10 alkylene group;

R is a substituted or unsubstituted phenyl group, naphthyl group, C3-20 cycloalkyl group, or C1-20 alkoxyl group;

$Q_1$ and $Q_2$ are identical or different, and are independently, hydrogen, halogen, a C1-20 alkyl group, a C2-20 alkenyl group, a C1-20 alkoxy group, a C6-20 aryl group, a C7-20 alkylaryl group, or a C7-20 arylalkyl group.

The present invention also provides a metallocene compound represented by the following Chemical Formula 2:

[Chemical Formula 2]

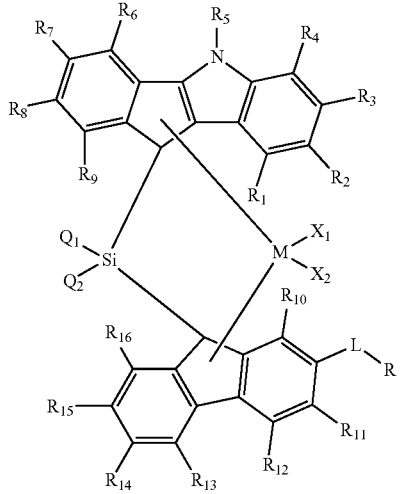

in the Chemical Formula 2,

M is a Group 4 transition metal;

$X_1$ and $X_2$ are identical or different, and are independently, halogen, a C1-20 alkyl group, a C2-20 alkenyl group, a C6-20 aryl group, a nitro group, an amido group, a C1-20 alkylsilyl group, a C1-20 alkoxy group, or a C1-20 sulfonate group;

$R_1$ to $R_{16}$ are identical or different, and are independently, hydrogen, halogen, a C1-20 alkyl group, a C2-20 alkenyl group, a C3-20 cycloalkyl group, a C4-20 cycloalkylalkyl group, a C1-20 alkoxy group, a C6-20 aryl group, a C5-20 heteroaryl group, a C7-20 alkylaryl group, or a C7-20 arylalkyl group, and two or more neighboring groups of $R_1$ to $R_{16}$ may be connected with each other to form a substituted or unsubstituted aliphatic or aromatic ring, provided that all of $R_1$ to $R_{16}$ are not hydrogen;

L is a direct bond or a C1-10 alkylene group;

R is a substituted or unsubstituted phenyl group, naphthyl group, C3-20 cycloalkyl group, or C1-20 alkoxyl group; and $Q_1$ and $Q_2$ are identical or different, and are independently, hydrogen, halogen, a C1-20 alkyl group, a C2-20 alkenyl group, a C1-20 alkoxy group, a C6-20 aryl group, a C7-20 alkylaryl group, or a C7-20 arylalkyl group.

The present invention also provides a method for preparing an olefin-based polymer, comprising a step of polymerizing olefin-based monomers in the presence of a catalyst composition comprising the above metallocene compound.

Advantageous Effects

The metallocene compound having new ligand may easily control the electronic, steric environment around metal by introducing various substituents into the ligand of connected indenoindoel derivative and fluorene derivative, and ultimately, may control the structure and properties of produced polyolefin.

The metallocene compound according to the present invention and a catalyst composition comprising the same may be used for olefin polymerization, and particularly, exhibit high activity even in copolymerization using comonomers, and may improve comonomer insertion capability, and thus, can be used to prepare olefin-based polymer having wide molecular weight distribution and the resulting excellent processability.

DETAILED DESCRIPTION OF THE EMBODIMENTS

As used herein, terms including an ordinal such as 'a first' or 'a second', and the like are used to explain various constitutional elements, and the terms are used only to distinguish one constitutional element from another constitutional element.

Unless otherwise described throughout the specification, technical terms are to mention specific embodiments, and do not intend to limit the present invention. And, the singular forms include the plural forms unless they have explicitly contrary meanings. And, the terms 'comprise', 'equipped with' or 'have' specify the existence of practiced properties, numbers, steps, constructional elements or combinations thereof, but do not exclude possibility of existence or addition of other properties, numbers, steps, constructional elements or combinations thereof.

And, in the present invention, in case it is described that each layer or element is formed "on" or "above" each layers or elements, it means that each layer or element is formed directly on the layers or elements, or that other layers or elements may be additionally formed between the layers, or on the subject or substrate.

Although various modifications can be made to the present invention and the present invention may be in various forms, specific examples will be illustrated and explained in detail below. However, these examples are not intended to limit the invention to specific disclosure, and it is to be understood that the present invention includes all the modifications, equivalents, or replacements within the idea and technical scope of the invention.

Hereinafter, the present invention will be explained in detail.

The ligand compound according to the present invention is represented by the following Chemical Formula 1.

[Chemical Formula 1]

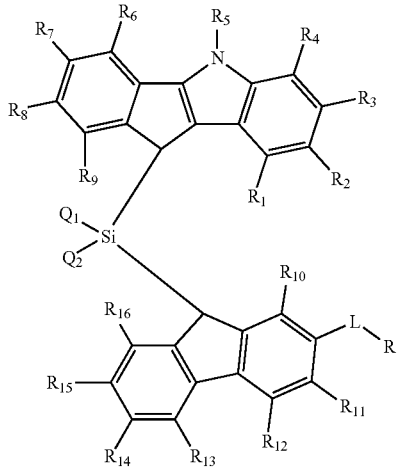

in the Chemical Formula 1, $R_1$ to $R_{16}$ are identical or different, and are independently, hydrogen, halogen, a C1-20 alkyl group, a C2-20 alkenyl group, a C3-20 cycloalkyl group, a C4-20 cycloalkylalkyl group, a C1-20 alkoxy group, a C6-20 aryl group, a C5-20 heteroaryl group, a C7-20 alkylaryl group, or a C7-20 arylalkyl group, and two or more neighboring groups of $R_1$ to $R_{16}$ may be connected with each other to form a substituted or unsubstituted aliphatic or aromatic ring, provided that all of $R_1$ to $R_{16}$ are not hydrogen;

L is a direct bond or a C1-10 alkylene group;

R is a substituted or unsubstituted phenyl group, naphthyl group, C3-20 cycloalkyl group, or C1-20 alkoxyl group;

$Q_1$ and $Q_2$ are identical or different, and are independently, hydrogen, halogen, a C1-20 alkyl group, a C2-20 alkenyl group, a C1-20 alkoxy group, a C6-20 aryl group, a C7-20 alkylaryl group, or a C7-20 arylalkyl group.

The main substituents in the Chemical Formula 1 will be explained in detail.

The C1-20 alkyl group may include a linear or branched alkyl group, and specifically, methyl, ethyl, propyl, isopropyl, n-butyl, tert-butyl, pentyl, hexyl, heptyl, octyl and the like, but is not limited thereto.

The C2-20 alkenyl group may include a linear or branched alkenyl group, and specifically, allyl, ethenyl, propenyl, butenyl, pentenyl and the like, but is not limited thereto.

The C6-20 aryl group may include an aryl group of a monocycle or fused ring, and specifically, phenyl, biphenyl, naphthyl, phenanthrenyl, fluorenyl and the like, but is not limited thereto.

The C5-20 heteroaryl group may include a heteroaryl group of a monocycle or fused rung, and specifically, carbozolyl, pyridyl, quinoline, isoquinoline, thiophenyl, furanyl, imidazole, oxazolyl, thiazolyl, triazine, tetrahydropyranyl, tetrahydrofuranyl and the like, but is not limited thereto.

The C1-20 alkoxy group may include methoxy, ethoxy, phenyloxy, cyclohexyloxy and the like, but is not limited thereto.

The C3-20 cycloalkyl group may include cyclopropyl, cyclobutyl, cyclopentyl, cyclohexyl and the like, but is not limited thereto.

The C4-20 cycloalkylalkyl group may include cyclopropylmethyl, cyclopropylethyl, cyclobutylmethyl, cyclobutylethyl, cyclopentylmethyl, cyclopentylethyl, cyclohexylmethyl, cyclohexylethyl and the like, but is not limited thereto.

According to one example of the invention, R of the Chemical Formula 1 may be phenyl, cyclopentyl, cyclohexyl, fluorophenyl or pentafluorophenyl. These functional groups may be introduced into the fluorene derivative of the ligand compound of one embodiment, and control the molecular weight and molecular weight distribution of prepared olefin polymer, and particularly, in case a phenyl, a cyclohexyl, a fluorophenyl, a pentafluorophenyl group and the like are used, the acid radical of central metal may increase to stabilize the ligand compound, thus improving catalytic activity. And, according to the substituents introduced into R in the Chemical Formula 1, the bite angle, defined as the angle of ligand, central metal and ligand may be controlled, and the above mentioned substituents may increase the bite angle of the compound of the Chemical Formula 1, thus facilitating the introduction of comonomers, and thereby, improving copolymerizability.

And, $R_2$ and $R_5$ of the Chemical Formula 1 may be identical to or different from each other, and independently, hydrogen or a C1-5 alkyl group.

Specific examples of the compound represented by the Chemical Formula 1 may include compounds represented by one of the following structural formulae, but are not limited thereto.

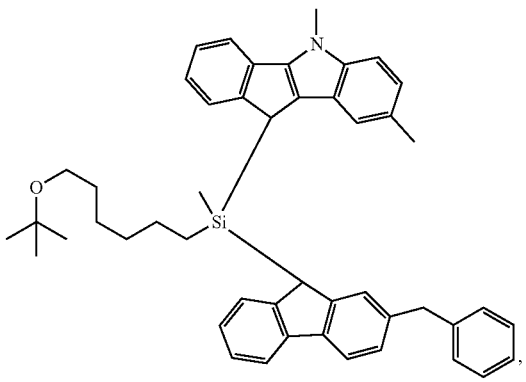

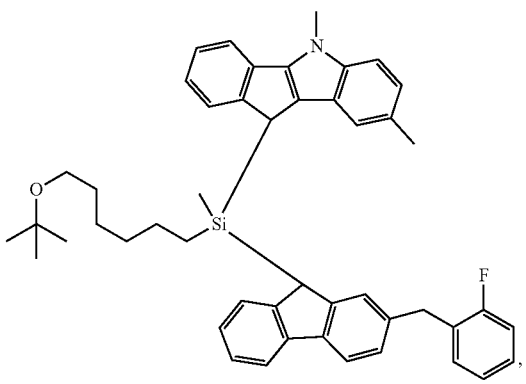

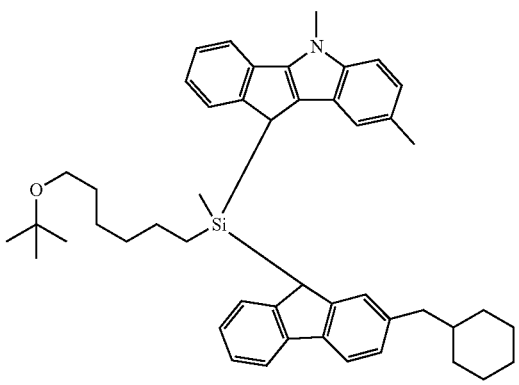

The compound represented by the Chemical Formula 1 may be synthesized as shown in the following Reaction Scheme 1.

[Reaction Scheme 1]

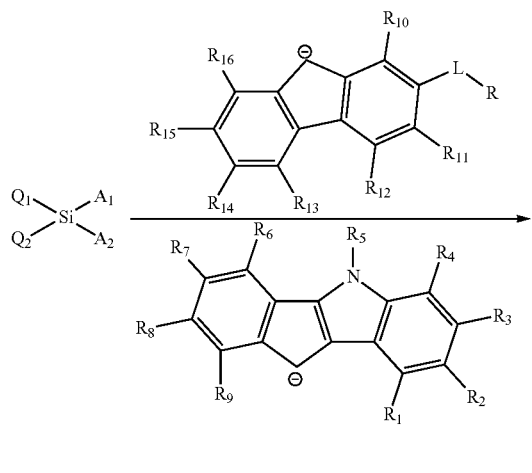

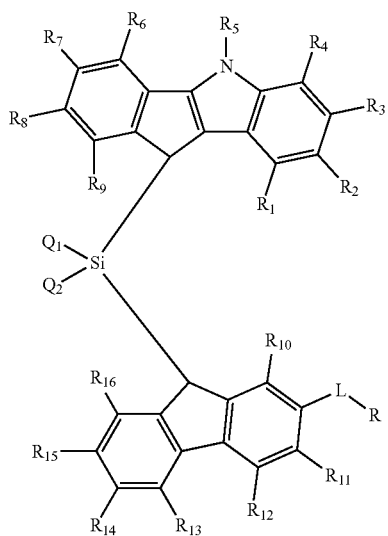

In the Reaction Scheme 1, R, $R_1$ to $R_{16}$, $Q_1$ and $Q_2$, L are as defined in the Chemical Formula 1, and $A_1$ and $A_2$ are halogen.

More specific examples will be described in the examples below, and one of ordinary skill in the art could prepare the compound of the Chemical Formula 1 referring to the description of the examples.

And, the ligand compound of the Chemical Formula 1 may be metalated with a transition metal to prepare a metallocene compound explained below.

Another aspect of the invention provides a metallocene compound represented by the following Chemical Formula 2.

[Chemical Formula 2]

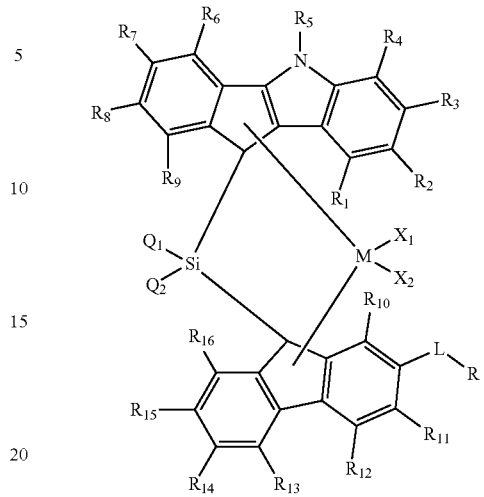

in the Chemical Formula 2,

M is a Group 4 transition metal;

$X_1$ and $X_2$ are identical or different, and are independently, halogen, a C1-20 alkyl group, a C2-20 alkenyl group, a C6-20 aryl group, a nitro group, an amido group, a C1-20 alkylsilyl group, a C1-20 alkoxy group, or a C1-20 sulfonate group;

$R_1$ to $R_{16}$ are identical or different, and are independently, hydrogen, halogen, a C1-20 alkyl group, a C2-20 alkenyl group, a C3-20 cycloalkyl group, a C4-20 cycloalkylalkyl group, a C1-20 alkoxy group, a C6-20 aryl group, a C5-20 heteroaryl group, a C7-20 alkylaryl group, or a C7-20 arylalkyl group, and two or more neighboring groups of $R_1$ to $R_{16}$ may be connected with each other to form a substituted or unsubstituted aliphatic or aromatic ring, provided that all of $R_1$ to $R_{16}$ are not hydrogen;

L is a direct bond or a C1-10 alkylene group;

R is a substituted or unsubstituted phenyl group, naphthyl group, C3-20 cycloalkyl group, or C1-20 alkoxyl group; and $Q_1$ and $Q_2$ are identical or different, and are independently, hydrogen, halogen, a C1-20 alkyl group, a C2-20 alkenyl group, a C1-20 alkoxy group, a C6-20 aryl group, a C7-20 alkylaryl group, or a C7-20 arylalkyl group.

The Group 4 transition metal may include titanium, zirconium, halfnium and the like, but is not limited thereto.

According to one example of the invention, R of the Chemical Formula 2 may be phenyl, cyclopentyl, cyclohexyl, fluorophenyl or pentafluorophenyl. These functional groups may be introduced into the fluorene derivative of the ligand compound of one embodiment, and control the molecular weight and molecular weight distribution of prepared olefin polymer, and particularly, in case a phenyl, a cyclohexyl, a fluorophenyl, a pentafluorophenyl group and the like are used, the acid radical of central metal may increase to stabilize the ligand compound, thus improving catalytic activity. And, according to the substituents introduced into R in the Chemical Formula 1, the bite angle, defined as the angle of ligand, central metal and ligand may be controlled, and the above mentioned substituents may increase the bite angle of the compound of the Chemical Formula 1, thus facilitating the introduction of comonomers, and thereby, improving copolymerizability.

And, $R_2$ and $R_5$ of the Chemical Formula 2 may be identical to or different from each other, and independently, hydrogen or a C1-5 alkyl group.

Specific examples of the metallocene compound represented by the Chemical Formula 2 may include those represented by one of the following structural formulae, but are not limited thereto.

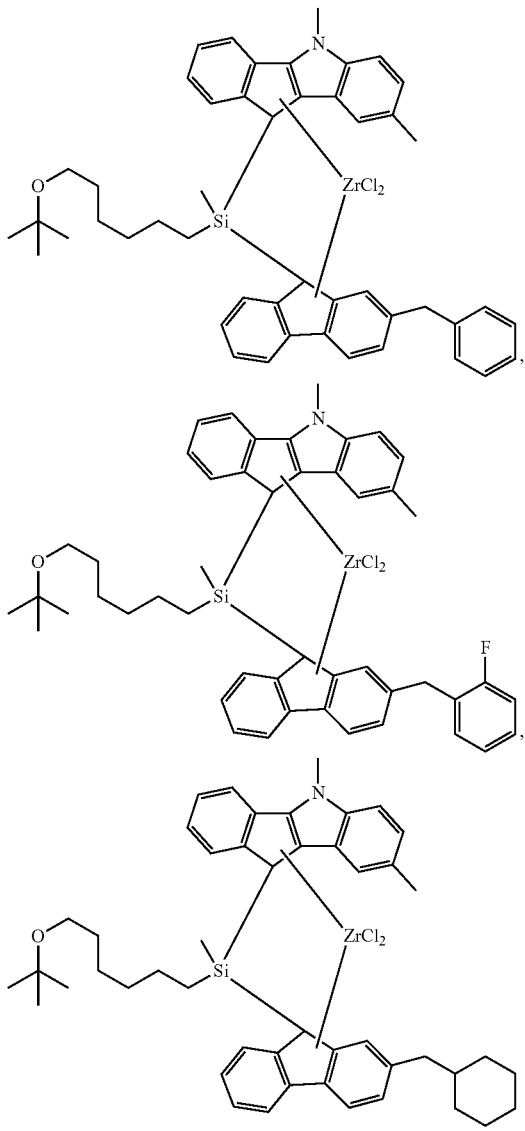

The metallocene compound of the Chemical Formula 2 has a basic backbone of an indeno indole derivative and a fluorene derivative, which form an asymmetrically cross-linked structure by a silicon bridge, and since unshared electron pair capable of acting as Lewis base exist in the ligand, it is supported on the carrier surface having Lewis acid property, thus exhibiting high polymerization activity even when supported. And, it has high activity by including electron-rich indeno indole group and fluorene group, and low hydrogen reactivity due to appropriate steric hindrance and the electronic effect of the ligand, maintaining high activity even when hydrogen exists. And, a nitrogen atom of the indeno indole derivative stabilizes beta-hydrogen of growing polymer chain by hydrogen bond, thus inhibiting beta-hydrogen elimination, and thus, an olefin-based polymer having a very high molecular weight can be polymerized.

And, the metallocene compound of one embodiment may introduce various substituents into the fluorene group, to control the molecular weight and molecular weight distribution of prepared olefin polymer according to the kind and the degree of bulkiness of the introduced substituents. According to one example of the invention, when R of the Chemical Formula 2 is a substituted or unsubstituted phenyl group, naphthyl group, C3-20 cycloalkyl group, or C1-20 alkoxy group, high copolymerization activity is exhibited, and comonomer insertion capability may be improved, and thus an olefin-based polymer having wide molecular weight distribution and high molecular weight may be prepared.

As such, since the metallocene compound of the present invention may have excellent activity and high copolymerizability, and be used to prepare polyolefin having high molecular weight and wide molecular weight distribution, thereby ultimately controlling the structure and properties of produced polyolefin.

The metallocene compound of the Chemical Formula 2 according to the present invention may be used as a catalyst for polymerization of olefin monomers.

The metallocene compound represented by the Chemical Formula 2 may be prepared by metalation of the ligand compound represented by the Chemical Formula 1 with a metal source, according to the following Reaction Scheme 2.

[Reaction Scheme 2]

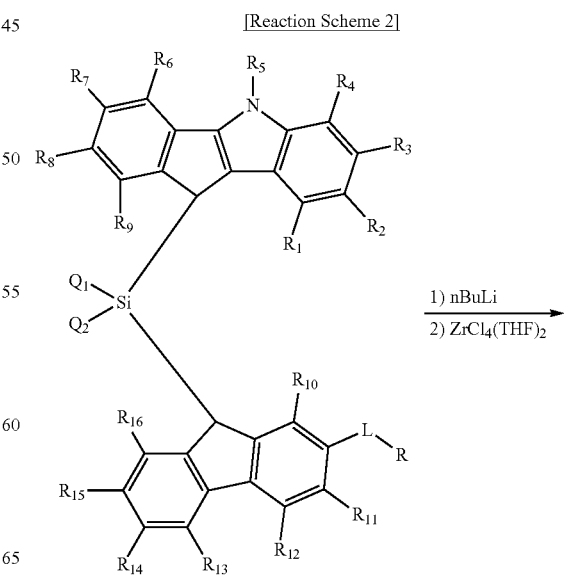

-continued

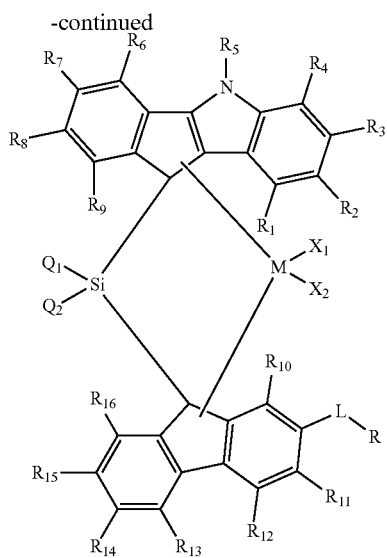

In the Reaction Scheme 2, R, $R_1$ to $R_{16}$, $Q_1$ and $Q_2$, L, $X_1$ and $X_2$ are the same as defined in the Chemical Formula 2.

More specific examples will be described in the examples below, and one of ordinary skill in the art could have prepared the metallocene compound of the Chemical Formula 2 referring to the description of the examples.

Another aspect of the invention provides a method for preparing an olefin-based polymer, comprising a step of polymerizing olefin-based monomers in the presence of a catalyst composition comprising the metallocene compound of the Chemical Formula 2.

The catalyst composition may further comprise at least one cocatalyst compound selected from the group consisting of a compound of the Chemical Formula 3, a compound of the Chemical Formula 4, and a compound of the Chemical Formula 5, in addition to the metallocene compound of the Chemical Formula 2.

—[Al($R_{17}$)—O]$n$-  [Chemical Formula 3]

in the Chemical Formula 3, $R_{17}$ is a halogen radical, a C1-20 hydrocarbyl radical, a C1-20 hydrocarbyl radical substituted with halogen, and n is an integer of 2 or more, D($R_{18}$)$_3$  [Chemical Formula 4]

in the Chemical Formula 4,

D is aluminum or boron, and $R_{18}$ is a C1-20 hydrocarbyl radical, or a C1-20 hydrocarbyl radical substituted with halogen,

[L-H]$^+$[Z$E_4$]$^-$ or [L]$^+$[Z$E_4$]$^-$  [Chemical Formula 5]

in the Chemical Formula 5,

L is neutral or cationic Lewis base, H is a hydrogen atom, Z is a Group 13 atom, and Es are identical or different, and are independently a C6-20 aryl group or a C1-20 alkyl group, where one or more hydrogen atoms are unsubstituted or substituted with halogen, a hydrocarbon having a carbon number of 1 to 20, alkoxy or phenoxy.

Among the cocatalyst compounds, the compound of the Chemical Formula 3 and the compound of the Chemical Formula 4 may be represented by an alkylating agent, and the compound of the Chemical Formula 5 may be represented by an activator.

The compound represented by the Chemical Formula 3 is not specifically limited as long as it is alkylaluminoxane, and preferable examples thereof may include methylaluminoxane, ethylaluminoxane, isobutylalumninoxane, butylaluminoxane, and the like, and preferably, methylaluminoxane may be used.

Although the alkyl metal compound represented by the Chemical Formula 4 is not specifically limited, preferable examples thereof may include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, and the like, and preferably, trimethylaluminum, triethylaluminum, triisobutylaluminum and the like may be used.

Examples of the compound represented by the Chemical Formula 5 may include triethylammoniumtetra(phenyl)boron, tributylammoniumtetra(phenyl)boron, trimethylammoniumtetra(phenyl)boron, tripropylammoniumtetra(phenyl)boron, trimethylammoniumtetra(p-tolyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetra(pentafluorophenyl)boron, N,N-diethylamilidiumtetra(phenyl)boron, N,N-diethylaniliniumtetra(phenyl)boron, N,N-diethylaniliniumtetra(pentafluorophenyl)boron, diethylammoniumtetra(pentafluorophenyl)boron, triphenylphosphoniumtetra(phenyl)boron, trimethylphosphoniumtetra(phenyl)boron, triethylammoniumtetra(phenyl)aluminum, tributylammoniumtetra(phenyl)aluminum, trimethylammoniumtetra(phenyl)aluminum, tripropylammoniumtetra(phenyl)aluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra(p-trifluoromethylphenyl)aluminum, tributylammoniumtetra(pentafluorophenyl)aluminum, N,N-diethylaniliniumtetra(phenyl)aluminum, N,N-diethylaniliniumtetra(phenyl)aluminum, N,N-diethylaniliniumtetra(pentafluorophenyl)aluminum, diethylammoniumtetra(pentafluorophenyl)aluminum, triphenylphosphoniumtetra(phenyl)aluminum, trimethylphosphoniumtetra(phenyl)aluminum, triethylammoniumtetra(phenyl)aluminum, tributylammoniumtetra(phenyl)aluminum, trimethylammoniumtetra(phenyl)boron, tripropylammoniumtetra(phenyl)boron, trimethylammoniumtetra(p-tolyl)boron, tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetra(pentafluorophenyl)boron, N,N-diethylaniliniumtetra(phenyl)boron, N,N-diethylaniliniumtetra(phenyl)boron, N,N-diethylaniliniumtetra(pentafluorophenyl)boron, diethylammoniumtetra(pentafluorophenyl)boron, triphenylphosphoniumtetra(phenyl)boron, triphenylcarboniumtetra(p-trifluoromethylphenyl)boron, triphenylcarboniumtetra(pentafluorophenyl)boron, trityltetra(pentafluorophenyl)boron, but not limited thereto.

And, the catalyst composition may be used for homopolymerization or copolymerization of olefins.

Meanwhile, as the method for preparing the catalyst composition according to the present invention, for example, the following methods may be used.

First, a preparation method comprising a step of contacting the metallocene compound of the Chemical Formula 2 and the compound of the Chemical Formula 3 and/or the compound of the Chemical Formula 4 to obtain a mixture; and adding the compound of the Chemical Formula 5 to the mixture may be used.

Second, a method of contacting the metallocene compound of the Chemical Formula 2 and the compound of the Chemical Formula 3 to prepare a catalyst composition may be used.

Third, a method of contacting the metallocene compound of the Chemical Formula 2 and the compound of the Chemical Formula 5 to prepare a catalyst composition may be used.

Among the preparation methods of a catalyst composition, in the case of the first method, the mole ratio of the metallocene compound of the Chemical Formula 2 to the compound of the Chemical Formula 3 and the compound of the Chemical Formula 4 may be 1:2 to 1:5,000, preferably 1:10 to 1:1,000, more preferably 1:20 to 1:500. And, the mole ratio of the metallocene compound of the Chemical Formula 2 to the compound of the Chemical Formula 5 may be 1:1 to 1:25, preferably 1:1 to 1:10, more preferably 1:2 to 1:5.

If the amount of the compound of the Chemical Formula 3 and the compound of the Chemical Formula 4 per one mole of the metallocene compound of the Chemical Formula 2 is less than 2 moles, the amount of an alkylating agent may be too small, and thus, alkylation of the metal compound may not be completely progressed. And, if the amount of the compound of the Chemical Formula 3 and the compound of the Chemical Formula 4 per one mole of the metallocene compound of the Chemical Formula 2 is greater than 5,000 moles, although alkylation of the metal compound is achieved, due to the side reaction between the excessive amount of remaining alkylation agent and the activator of the Chemical Formula 5, activation of the metal compound may not be completely achieved. And, if the amount of the compound of the Chemical Formula 5 per 1 mole of the metallocene compound of the Chemical Formula 2 is less than 1 mole, the amount of the activator may be relatively small, and thus, activation of the metal compound may not be completely achieved, thus decreasing activity of the catalyst composition, and if the amount of the compound of the Chemical Formula 5 per 1 mole of the metallocene compound of the Chemical Formula 2 is greater than 25 moles, although activation of the metal compound is completely achieved, due to the excessive amount of remaining activator, unit cost of the catalyst composition may not be economical or purity of produced polymer may be lowered.

Among the preparation methods of a catalyst composition, in the case of the second method, the mole ratio of the metallocene compound of the Chemical Formula 2 to the compound of the Chemical Formula 3 may be 1:10 to 1:10,000, preferably 1:100 to 1:5,000, more preferably 1:500 to 1:2,000. If the amount of the compound of the Chemical Formula 3 per 1 mole of the metallocene compound of the Chemical Formula 2 is less than 10 moles, the amount of an activator may be relatively small, and thus, activation of the metal compound may not be completely achieved, thus decreasing activity of the catalyst composition, and if the amount of the compound of the Chemical Formula 3 per 1 mole of the metallocene compound of the Chemical Formula 2 is greater than 10,000 moles, although activation of the metal compound is completely achieved, due to the excessive amount of remaining activators, unit cost of the catalyst composition may not be economical or purity of produced polymer may be lowered.

Among the preparation methods of a catalyst composition, in the case of the third method, the mole ratio of the metallocene compound of the Chemical Formula 2 to the compound of the Chemical Formula 5 may be 1:1 to 1:25, preferably 1:1 to 1:10, more preferably 1:2 to 1:5.

When preparing the catalyst composition, hydrocarbon solvents such as pentane, hexane, heptanes and the like, or aromatic solvents such as benzene, toluene and the like may be used as a reaction solvent, but all solvents that can be used in the field may be used without limitations.

The method for preparing an olefin-based polymer according to the present invention may be conducted by contacting the catalyst composition with monomers. According to the method for preparing an olefin polymer, an olefin homopolymer or an olefin copolymer may be provided.

The polymerization method of the present invention may be conducted by a solution polymerization process, a slurry process or a gas phase process.

In the method for preparing polymer according to the present invention, the catalyst composition may be dissolved or diluted in C5-12 aliphatic hydrocarbon solvents, for example, pentane, hexane, heptanes, nonane, decane, and isomers thereof, aromatic hydrocarbon solvents such as toluene, benzene, hydrocarbon solvents substituted with a chlorine atom such as dichloromethane, chlorobenzene, and the like, which are suitable for olefin polymerization, before introduction. The solvent may be preferably treated with a small amount of alkylaluminium, thereby removing a small amount of water or air acting as a catalyst poison, before use, and a cocatalyst may be further used.

Examples of olefin-based monomers that can be polymerized using the metallocene compounds and cocatalyst may include ethylene, alpha-olefin, cyclic olefin, and the like, and diene olefin-based monomers or triene olefin-based monomers having two or more double bonds may be also polymerized. Specific examples of the monomers may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene, norbornene, norborndiene, ethylidenenorbornene, phenylnorbornene, vinylnorbornene, dicyclopentadiene, 1,4-butadiene, 1,5-pentadiene, 1,6-hexadiene, styrene, alpha-methylstyrene, divinylbenzene, 3-chlorormethylstyrene, and the like, two or more kinds of these monomers may be mixed and copolymerized. In case the olefin polymer is copolymer of ethylene with another comonomer, the monomer constituting the copolymer may be preferably at least one comonomer selected from the group consisting of propylene, 1-butene, 1-hexene and 4-methyl-1-pentene, and 1-octene.

Particularly, in the preparation method of olefin polymer according to the present invention, the catalyst composition may be used for copolymerization of ethylene with monomers having large steric hindrance such as 1-hexene and 1-octene, and by introducing various substituents into the basic backbone of fluorene derivative, electronic, steric environment around the metal may be easily controlled, and ultimately, the structure and the properties of produced polymer may be controlled.

According to one example of the invention, the olefin-based polymer may have weight average molecular weight (Mw) of about 100,000 to 1,000,000 g/mol. The weight average molecular weight of the olefin-based polymer may vary according to the metallocene compound used, and whether or not a catalyst composition comprising the same is supported, or polymerization conditions, and for example, olefin-based polymer prepared using a supported catalyst may have very high weight average molecular weight of 800,000 g/mol or more, preferably 850,000 g/mol or more.

And, the olefin-based polymer may have molecular weight distribution (PDI) of about 1 to 20, preferably about 1 to 10.

Hereinafter, a polymerization process of olefin polymer will be exemplified. However, these are presented only to illustrate the invention, and are not intended to limit the scope of the invention thereto.

A reactor used in the preparation method of polymer according to the present invention may be preferably a continuously stirred tank reactor (CSTR) or a continuous flow reactor (PFR). It is preferable that two or more of the reactors are arranged in series or in a row. And, it is preferable that the preparation method further comprises a separator for continuously separating solvents and non-reacted monomers from a reaction mixture.

In case the preparation method of polymer according to the present invention is conducted by a continuous solution polymerization process, it may consist of a catalytic process, a polymerization process, a solvent separation process and a recovery process, which will be explained below in detail.

a) A Catalytic Process

The catalyst composition according to the present invention may be dissolved or diluted in a C5-12 aliphatic or aromatic solvent unsubstituted or substituted with halogen, which is suitable for olefin polymerization, before introduction. For example, an aliphatic hydrocarbon solvent such as pentane, hexane, heptane, nonane, decane, and isomers thereof, an aromatic hydrocarbon solvent such as toluene, xylene and benzene, a hydrocarbon solvent substituted with a chlorine atom such as dichloromethane and chlorobenzene, and the like may be used. It is preferable that the solvent is treated with a small amount of alkylaluminum and the like, thereby removing a small amount of water or air and the like, which acts as a catalyst poison, and an excessive amount of a cocatalyst may be used.

b) A Polymerization Process

A polymerization process is progressed by introducing a catalyst composition comprising the organic metallocene compound of the Chemical Formula 2 and a cocatalyst and at least one kind of olefin monomers in a reactor. In the case of solution and slurry polymerization, a solvent is introduced in the reactor. In the case of solution polymerization, a mixed solution of a solvent, a catalyst composition and monomers exist inside a reactor.

The mole ratio of monomers to solvent should be suitable for dissolving raw material before the reaction and polymer produced after the reaction. Specifically, the mole ratio of monomers to solvent may be 10:1 to 1:10,000, preferably 5:1 to 1:100, most preferably 1:1 to 1:20. If the mole ratio is less than 10:1, the amount of solvents may be too small, and thus, viscosity of fluid may increase to cause problems in terms of polymer transfer, and if the mole ratio is greater than 1:10,000, the amount of the solvent may be more than is necessary, thus increasing facilities and energy cost and the like due to purification and recycle of the solvent.

It is preferable that the solvent is introduced into the reactor at a temperature of −40° C. to 150° C. using a heater or a refrigerator, and thus, a polymerization reaction begins with the monomers and the catalyst composition. If the temperature of the solvent is less than −40° C., although it differs according to the reaction amount, in general, the temperature of the solvent is too low, and thus, reaction temperature may drop together, rendering it difficult to control the temperature, and if it is greater than 150° C., the temperature of the solvent is too high, thus rendering it difficult to remove reaction heat.

As a high capacity pump increases pressure above 50 bar to supply feed (solvent, monomers, catalyst composition, and the like), a feed mixture may be passed without additional pumping between the reactor arrangement, a pressure dropping device and a separator.

The internal temperature of the reactor, i.e., polymerization temperature suitable for the present invention is −15° C. to 300° C., preferably 30° C. to 200° C., most preferably 70° C. to 200° C. If the internal temperature is less than −15° C., productivity may be decreased due to low reaction speed, and if it is greater than 300° C., due to side reactions, discoloration problem such as polymer carbonization and generation of impurities may be caused.

The internal pressure of the reactor suitable for the present invention is 1 bar to 300 bar, preferably 10 to 200 bar, most preferably 30 to 100 bar. If the internal pressure is less than 1 bar, productivity may be decreased due to low reaction speed, and the solvent may be vaporized, and if it is greater than 300 bar, the cost of equipment such as device cost due to high pressure may increase.

It is preferable that the polymer produced in the reactor is maintained in the solvent at a concentration less than 20 wt %, and after a short residence time, is transferred to a first solvent separation process for solvent removal. The residence time of the produced polymer in the reactor may be 1 minute to 10 hours, preferably 3 minutes to 1 hour, most preferably 5 minutes to 30 minutes. If the residence time is less than 3 minutes, due to the short residence time, productivity may be decreased and catalyst may be lost, thus increasing preparation cost, and if it is greater than 1 hour, due to reaction for more than optimum active period of a catalyst, a reactor may become larger, thus increasing the cost of equipment.

c) A Solvent Separation Process

By changing the temperature and the pressure of the solution to remove the solvent existing together with the polymer coming out of the reactor, a solvent separation process is conducted. For example, the temperature of a polymer solution transferred from a reactor is raised to about 200° C. to about 230° C. through a heater, and then, the pressure is dropped while passing through a pressure dropping device, and non-reacted raw material and the solvent are vaporized in a first separator.

Wherein, the pressure inside the separator may be 1 to 30 bar, preferably 1 to 10 bar, most preferably 3 to 8 bar. The temperature inside the separator may be 150° C. to 250° C., preferably 170° C. to 230° C., most preferably 180° C. to 230° C.

If the pressure inside the separator is less than 1 bar, polymer content may increase, thus causing a problem in terms of transfer, and if it is greater than 30 bar, it may be difficult to separate the solvent used in the polymerization process. And, if the temperature inside the separator is less than 150° C., the viscosity of copolymer and a mixture thereof may increase, thus causing a problem in terms of transfer, and if it is greater than 250° C., degeneration may occur due to the high temperature, thus causing carbonization and the resulting discoloration of polymer.

The solvent vaporized in the separator may be recycled to a condensed reactor in overhead system. After passing through the first solvent separation process, a polymer solution concentrated to 65% may be obtained, which is transferred to a second separator by a transfer pump through a heater, and a separation process for the remaining solvent is conducted in a second separator. In order to prevent modification of polymer due to high temperature while passing through the heater, a heat stabilizer is introduced, and simultaneously, in order to inhibit the reaction of polymer due to the remaining activity of activated substance existing in the polymer solution, a reaction inhibitor is introduced into the heater together with the heat stabilizer. The remaining solvent in the polymer solution introduced into the second separator is finally removed completely by a vacuum pump, and after passing through a coolant and a cutter, granulated polymer may be obtained. The solvent vaporized in the second separation process and other non-reacted monomers may be sent to a recovery process, and purified and reused.

d) A Recovery Process

The organic solvent introduced together with raw material in the polymerization process may be recycled to the polymerization process together with non-reacted raw material in the first solvent separation process. However, it is preferable that the solvent recovered in the second solvent separation process is purified in a recovery process and reused, because the incorporation of a reaction inhibitor cause pollution and moisture acting as a catalyst poison may be contained in the solvent in a large quantity due to steam supply in a vacuum pump.

Hereinafter, the present invention will be explained in detail with reference to the following examples. However, these examples are only to illustrate the invention, and the scope of the invention is not limited thereto.

EXAMPLE

The term "overnight" means about 12 to 16 hours, and "room temperature" or "ambient temperature" refers to a temperature of 20 to 25° C. All the syntheses of metal compounds and preparation of experiments were conducted under argon (Ar) atmosphere using dry box technique or using glass apparatus maintaining a dry state. All solvents used were anhydrous grades and dried before use.

Preparation Example of a Ligand Compound and a Metallocene Compound

Preparation Example 1

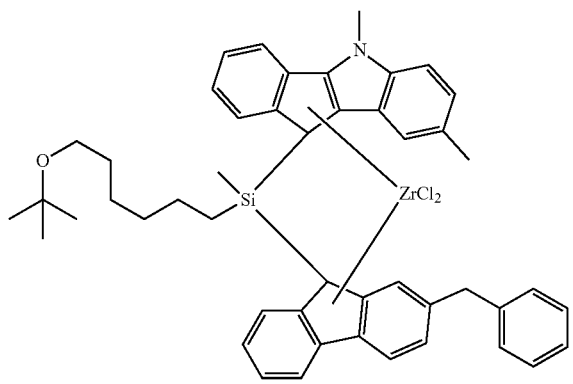

(1) Preparation of a Ligand Compound:

2.56 g (10 mmol) of 2-Benzyl-9H-fluorene (BnFlu) was dissolved in 100 ml of hexane, 4.17 ml (3.5 eq) of MTBE, and 4.6 ml (11.5 mmol) of n-BuLi, 2.5M solution in hexane was added thereto dropwise in a dryice/acetone bath. And, after reacting at room temperature overnight, yellow slurry was obtained. In a glove box, 2.98 g (11 mmol) of a Si-tether bridge compound was prepared to make 100 ml of the hexane solution, and the BnFlu-Li solution was fed thereto dropwise in a dryice/acetone bath. It was confirmed that the solution turned violet by stirring at room temperature overnight (BnFlu-Si-tether).

2.33 g (10 mmol) of Indenoindole (InIn) was dissolved in 50 ml of THF, and 4.6 ml (11.5 mmol) of n-BuLi, 2.5M solution in hexane was added thereto dropwise in a dryice/acetone bath. And, after reacting at room temperature overnight, red slurry was obtained. To the above prepared BnFlu-Si-tether slurry, the InIn—Li solution was fed dropwise in a dryice/acetone bath. It was confirmed that the solution turned dark brown by stirring at room temperature overnight. And, after water/ether work-up, 6.5 g of sticky oil was obtained (yield: 94.5%).

$^1$H NMR (500 MHz, CDCl$_3$): −0.35-−0.13 (3H, m), 0.23-1.57 (19H, m), 2.35-2.45 (3H, m), 3.21-3.27 (2H, m), 3.92-4.01 (2H, m), 4.03-4.11 (5H, m), 7.05-7.83 (19H, m)

(2) Preparation of a Metallocene Compound:

4.82 g (7 mmol) of the ligand compound synthesized in (1) was dissolved in 100 mL of toluene, 3.3 ml (4.0 eq.) of MTBE was additionally added thereto, and to the solution, 6.2 mL of n-BuLi, 2.5M solution in hexane was added dropwise in a dry ice/acetone bath, and the solution was stirred at room temperature overnight to obtain reddish slurry. In a glove box, 2.64 g (7 mmol) of ZrCl$_4$(THF)$_2$ was prepared to make 100 mL of the toluene solution, and the ligand-Li solution was fed thereto dropwise in a dry ice/acetone bath. And, it was confirmed that the solution turned violet by stirring at room temperature overnight. About 80% of toluene was vacuum dried, and the solution was recrystallized with hexane, and the slurry was filtered to obtain 3.62 g of a dark violet metallocene compound (yield: 61%).

$^1$H NMR (500 MHz, CDCl$_3$): 0.80-2.28 (22H, m), 2.43 (3H, d), 3.28-3.32 (2H, m), 3.78-3.84 (3H, d), 3.90 (3H, s), 6.62-7.90 (19H, m)

Preparation Example 2

(1) Preparation of a Ligand Compound:

1.84 g (7 mmol) 2-(cyclohexylmethyl)-9H-fluorene (CyhexmeFlu) was dissolved in 100 ml of hexane, 2.92 ml (3.5 eq) of MTBE, and 3.2 ml (8.1 mmol) of n-BuLi, 2.5M solution in hexane was added thereto dropwise in a dryice/acetone bath. And, after reacting at room temperature overnight, orange slurry was obtained. In a glove box, 2.09 g (7.7 mmol) of a Si-tether bridge compound was prepared to make 100 ml of a hexane solution, and the CyhexmeFlu-Li solution was fed thereto dropwise in a dryice/acetone bath. It was confirmed that the solution turned violet by stirring at room temperature overnight (CyhexmeFlu-Si-tether).

1.63 g (7 mmol) of Indenoindole (InIn) was dissolved in 50 ml of THF, and 3.2 ml (8.1 mmol) of n-BuLi, 2.5M solution in hexane was added thereto dropwise in a dryice/acetone bath. And, after reacting at room temperature overnight, burgundy slurry was obtained. To the above prepared CyhexmeFlu-Si-tether slurry, the InIn—Li solution was fed dropwise in a dryice/acetone bath. It was confirmed that the solution turned dark brown by stirring at room temperature overnight. And, after water/ether work-up, 4.86 g of sticky oil was obtained (yield: 100%).

$^1$H NMR (500 MHz, CDCl$_3$): −0.36--−0.23 (3H, m), 0.15-1.70 (29H, m), 1.98-2.06 (1H, m), 2.39-2.42 (3H, m), 2.55-2.60 (2H, m), 3.19-3.23 (2H, m), 3.96 (1H, d), 4.08-4.09 (3H, m), 4.11-4.13 (1H, m), 7.05-7.83 (14H, m)

(2) Preparation of a Metallocene Compound:

4.76 g (7 mmol) of the ligand compound synthesized in (1) was dissolved in 100 mL of toluene, 3.3 ml (4.0 eq.) of MTBE was additionally added thereto, and to the solution, 6.2 Ml of n-BuLi, 2.5M solution in hexane was added dropwise in a dry ice/acetone bath, and the solution was stirred at room temperature overnight to obtain reddish slurry. In a glove box, 2.64 g (7 mmol) of ZrCl$_4$(THF)$_2$ was prepared to make 100 mL of the toluene solution, and the ligand-Li solution was fed thereto dropwise in a dry ice/acetone bath. It was confirmed that the solution turned dark violet by stirring at room temperature overnight. About 80% of toluene was vacuum dried, the solution was recrystallized with hexane, and the slurry was filtered to obtain 2.89 g of a dark purple metallocene compound (yield: 49.1%)

$^1$H NMR (500 MHz, CDCl$_3$): 0.84-2.20 (32H, m), 2.58 (3H, d), 3.37-3.41 (2H, m), 3.92 (3H, s), 6.63-7.94 (14H, m)

Preparation Example 3

It was confirmed that the solution turned violet by stirring at room temperature overnight (2-FBnFlu-Si-tether).

2.33 g (10 mmol) of Indenoindole (InIn) was dissolved in 50 ml of THF, and 4.6 ml (11.5 mmol) of n-BuLi, 2.5M solution in hexane was added thereto dropwise in a dryice/acetone bath. And, after reacting at room temperature overnight, burgundy slurry was obtained. To the above prepared 2-FBnFlu-Si-tether slurry, the InIn—Li solution was fed dropwise in a dryice/acetone bath. It was confirmed that the solution turned violet by stirring at room temperature overnight. And, after water/ether work-up, 6.75 g of sticky oil was obtained (yield: 95.6%).

$^1$H NMR (500 MHz, CDCl$_3$): −0.39--−0.19 (3H, m), 0.16-1.54 (19H, m), 2.35-2.44 (3H, m), 3.20-3.25 (2H, m), 3.93-4.01 (3H, m), 4.02-4.08 (4H, m), 6.96-7.81 (18H, m)

(2) Preparation of a Metallocene Compound:

6.75 g (9.6 mmol) of the ligand compound synthesized in (1) was dissolved in 100 mL of toluene, and 4.6 ml (4.0 eq.) of MTBE was additionally added thereto, and to the solution, 8.4 ml (2.2 eq.) of n-BuLi, 2.5M solution in hexane was added dropwise in a dry ice/acetone bath, and the solution was stirred at room temperature overnight to obtain reddish slurry. In a glove box, 3.61 g (9.6 mmol) of ZrCl$_4$(THF)$_2$ was prepared to make 100 mL of the toluene solution, and the ligand-Li solution was fed thereto dropwise in a dry ice/acetone bath. And, it was confirmed that the solution turned dark red by stirring at room temperature overnight. About 80% of toluene was vacuum dried, the solution was recrystallized with hexane, and the slurry was filtered to obtain 5.45 g of a reddish brown metallocene compound (yield: 64.3%).

$^1$H NMR (500 MHz, CDCl$_3$): 1.17-1.20 (12H, m), 1.47-2.35 (10H, m), 2.45-2.57 (3H, m), 3.35-3.40 (2H, m), 3.74-4.00 (5H, m), 6.82-7.93 (18H, m)

Preparation Comparative Example 1

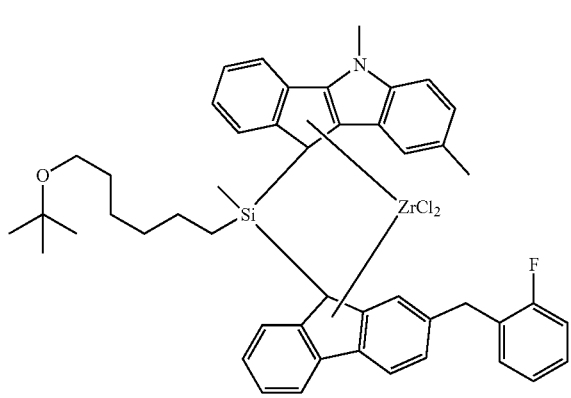

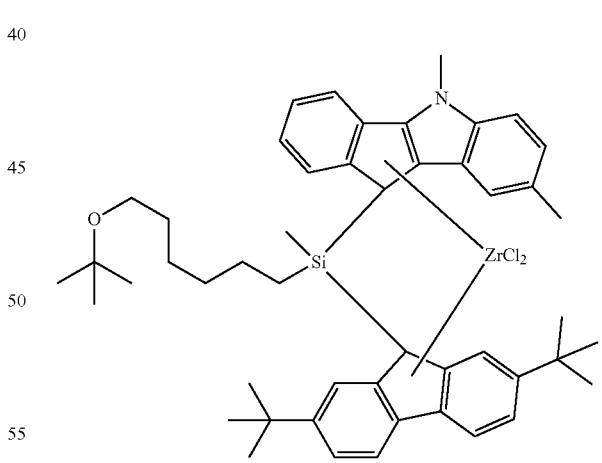

(1) Preparation of a Ligand Compound:

2.74 g (10 mmol) of 2-(2-Fluorobenzyl)-9H-fluorene (2-FBnFlu) was dissolved in 100 ml of hexane, 4.17 ml (3.5 eq.) of MTBE, and 4.6 ml (11.5 mmol) of n-BuLi, 2.5M solution in hexane was added thereto dropwise in a dryice/acetone bath. And, after reacting at room temperature overnight, burgundy slurry was obtained. In a glove box, 2.98 g (11 mmol) of a Si-tether bridge compound was prepared to make 100 ml of the hexane solution, and the 2-FBnFlu-Li solution was fed thereto dropwise in a dryice/acetone bath.

(1) Preparation of a Ligand Compound:

1.95 g (7 mmol) of 2,7-Bis(1,1-dimethylethyl)-9H-fluorene (tBuFlu) was dissolved in 100 ml of hexane, 2.92 ml (3.5 eq.) of MTBE, and 3.2 ml (8.1 mmol) of n-BuLi, 2.5M solution in hexane was added thereto dropwise in a dryice/acetone bath. And, after reacting at room temperature overnight, reddish brown slurry was obtained. In a glove box, 2.09 g (7.7 mmol) of a Si-tether bridge compound was prepared to make 100 ml of the hexane solution, and the tBuFlu-Li solution was fed thereto dropwise in a dryice/ acetone bath. It was confirmed that the solution turned violet by stirring at room temperature overnight (tBuFlu-Si-tether).

1.63 g (7 mmol) of Indenoindole (InIn) was dissolved in 50 ml of THF, and 3.2 ml (8.1 mmol) of n-BuLi, 2.5M solution in hexane was added thereto dropwise in a dryice/acetone bath. And, after reacting at room temperature overnight, burgundy slurry was obtained. To the above prepared tBuFlu-Si-tether slurry, the InIn—Li solution was fed dropwise in a dryice/acetone bath. It was confirmed that the solution turned violet by stirring at room temperature overnight. And, after water/ether work-up, 4.86 g of sticky oil was obtained (yield: 100%).

$^1$H NMR (500 MHz, d6-benzene): −0.30−−0.18 (3H, d), 0.40 (2H, m), 0.65-1.45 (8H, m), 1.12 (9H, d), 1.29-1.31 (18H, d), 2.36-2.40 (3H, d), 3.17 (2H, m), 3.41-3.43 (3H, d), 4.17-4.21 (1H, d), 4.34-4.38 (1H, d), 6.90-7.80 (13H, m)

(3) Preparation of a Metallocene Compound:

4.97 g (7 mmol) of the ligand compound synthesized in (1) was dissolved in 100 mL of toluene, 3.3 ml (4.0 eq.) of MTBE was additionally added thereto, and to the solution, 6.2 mL of n-BuLi, 2.5M solution in hexane was added dropwise in a dry ice/acetone bath, and the solution was stirred at room temperature overnight to obtain reddish slurry. In a glove box, 2.64 g (7 mmol) of ZrCl$_4$(THF)$_2$ was prepared to make 100 mL of the toluene solution, and the ligand-Li solution was fed thereto dropwise in a dry ice/acetone bath. And, it was confirmed that the solution turned dark violet by stirring at room temperature overnight. About 80% of toluene was vacuum dried, and then, the solution was recrystallized with hexane, and the slurry was filtered to obtain 5.22 g of a dark violet metallocene compound (yield: 85.7%).

$^1$H NMR (500 MHz, CDCl$_3$): 0.96-1.22 (18H, d), 1.19 (9H, d), 1.71 (3H, d), 1.50-1.70 (4H, m), 1.79 (2H, m), 1.98-2.19 (4H, m), 2.58 (3H, s), 3.38 (2H, m), 3.91 (3H, d), 6.66-7.88 (13H, m)

Preparation Comparative Example 2

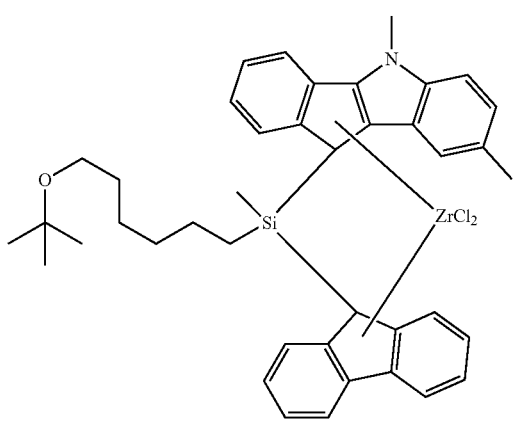

(1) Preparation of a Ligand Compound:

2 g of fluorene was dissolved in 5 ml of MTBE, 100 ml of hexane, and 5.5 ml of n-BuLi, 2.5M solution in hexane was added thereto dropwise in a dry ice/acetone bath, and the solution was stirred at room temperature overnight. And, 3.6 g of (6-(tert-butoxy)hexyl)dichloro(methyl)silane was dissolved in 50 ml of hexane, the fluorene-Li slurry was transferred thereto for 30 minutes in a dry ice/acetone bath, and the solution was stirred at room temperature overnight.

Simultaneously, 5,8-dimethyl-5,10-dihydroindeno[1,2-b]indole (12 mmol, 2.8 g) was dissolved in 60 ml of THF, and 5.5 ml of n-BuLi, 2.5M solution in hexane was added thereto dropwise in a dryice/acetone bath, and the solution was stirred at room temperature overnight.

The reaction solution of fluorene and (6-(tert-butoxy) hexyl)dichloro(methyl)silane was NMR-sampled to confirm the completion of the reaction, and then, the 5,8-dimethyl-5,10-dihydroindeno[1,2-b]indole-Li solution was transferred thereto under a dry ice/acetone bath. The solution was stirred at room temperature overnight, and after the reaction, extracted with ether/water to remove remaining water of the organic layer with MgSO$_4$, thus obtaining a ligand compound (Mw 597.90, 12 mmol), and it was confirmed by 1H-NMR that two isomers were produced.

$^1$H NMR (500 MHz, d6-benzene): −0.30−−0.18 (3H, d), 0.40 (2H, m), 0.65-1.45 (8H, m), 1.12 (9H, d), 2.36-2.40 (3H, d), 3.17 (2H, m), 3.41-3.43 (3H, d), 4.17-4.21 (1H, d), 4.34-4.38 (1H, d), 6.90-7.80 (15H, m)

(2) Preparation of a Metallocene Compound:

7.2 g (12 mmol) of the ligand compound synthesized in (1) was dissolved in 50 mL of diethylether, and 11.5 mL of n-BuLi, 2.5M solution in hexane was added thereto dropwise in a dry ice/acetone bath, and the solution was stirred at room temperature overnight to obtain brown sticky oil. It was dissolved in toluene to prepare slurry. And, 50 mL of toluene was introduced in ZrCl$_4$(THF)$_2$ to prepare ZrCl$_4$(THF)$_2$ toluene slurry, and 50 mL of the ZrCl$_4$(THF)$_2$ toluene slurry was transferred under a dry ice/acetone bath. And it was confirmed that the slurry turned violet by stirring at room temperature overnight. After the reaction, the reaction solution was filtered to remove LiCl, and toluene of the filtrate was vacuum dried to remove, and then, hexane was introduced and sonication was conducted for 1 hour. The slurry was filtered to obtain 6 g of filtered solid, a dark violet metallocene compound (Mw 758.02, 7.92 mmol, yield 66 mol %), and it was confirmed by 1H-NMR that two isomers were produced.

$^1$H NMR (500 MHz, CDCl$_3$): 1.19 (9H, d), 1.71 (3H, d), 1.50-1.70 (4H, m), 1.79 (2H, m), 1.98-2.19 (4H, m), 2.58 (3H, s), 3.38 (2H, m), 3.91 (3H, d), 6.66-7.88 (15H, m)

Preparation Example 4

Preparation of a Supported Catalyst

Silica (manufactured by Grace Davison Company, SYLOPOL 948) was dehydrated at 400° C. for 12 hours under vacuum to prepare a silica support.

Into a glass reactor of room temperature, 100 mL of a toluene solution was introduced, and 10 g of the above prepared silica support was introduced, and then, the mixture was stirred while increasing the temperature of the reactor to 40° C. After the silica was sufficiently dispersed, 60.6 mL of a solution of 10 wt % methylaluminoxane (MAO)/toluene was introduced, and the temperature was raised to 80° C., and then, the mixture was stirred at 200 rpm for 16 hours. Thereafter, the temperature was lowered again to 40° C., and then, the solution was washed with a sufficient amount of toluene to remove unreacted aluminum compound. 100 mL of toluene was introduced again, 0.5 mmol of the metallocene compound prepared in the Preparation Example 1 was introduced, and the mixture was stirred for 2 hours. After the reaction, stirring was discontinued, a toluene layer was separated and removed, and then, remaining toluene was removed by pressure reduction at 40° C., thereby preparing a supported catalyst.

Preparation Example 5

Preparation of a Supported Catalyst

A supported catalyst was prepared by the same method as Preparation Example 4, except that 0.5 mmol of the metallocene compound prepared in the Preparation Example 2 was used.

Preparation Example 6

Preparation of a Supported Catalyst

A supported catalyst was prepared by the same method as Preparation Example 4, except that 0.5 mmol of the metallocene compound prepared in the Preparation Example 3 was used.

Preparation Comparative Example 3

Preparation of a Supported Catalyst

A supported catalyst was prepared by the same method as Preparation Example 4, except that 0.5 mmol of the metallocene compound prepared in the Preparation Comparative Example 1 was used.

Preparation Comparative Example 4

Preparation of a Supported Catalyst

A supported catalyst was prepared by the same method as Preparation Example 4, except that 0.5 mmol of the metallocene compound prepared in the Preparation Comparative Example 2 was used.

Examples of ethylene-1-hexene copolymerization

Example 1

Solution Polymerization

A 100 mL Andrew bottle was prepared and assembled with an impeller part, and then, the inside was replaced with argon in a glove box. Into the Andrew bottle, 70 mL of toluene containing a small amount of TMA was introduced and 10 mL of MAO solution (10 wt % in toluene) was added. 5 mL of a solution of catalyst/toluene (catalyst 5 µmol), which was prepared by dissolving the metallocene compound of the Preparation Example 1 in toluene, was introduced in to the Andrew bottle. While the Andrew bottle was immersed in an oil bath heated to 90° C., the top of the bottle was fixed to a mechanical stirrer, and then, the reaction solution was stirred for 5 minutes until it reached to 90° C. 5 mL of comonomer 1-hexen was introduced, the inside of the bottle was purged three times with ethylene gas, and then, the ethylene valve was opened to slowly pressurize. Ethylene was continuously supplied as much as consumed ethylene so as to maintain pressure, and the mechanical stirrer was operated to react at 500 rpm for 30 minutes. After the reaction was completed, temperature was lowered to room temperature, and the ethylene valve was closed and stirring was discontinued, and then, the pressure inside the reactor was slowly vented. 400 mL of the reactant was poured into a mixed solution of ethanol/HCl aqueous solution, and the solution was stirred for about 1 hour, and then, filtered to obtain polymer, which was dried in a vacuum oven of 60° C. for 20 hours. The weight of the obtained polymer was measured to calculate the activity of the catalyst, and 10 mg of the sample was taken and used for GPC analysis.

Example 2

Solution Polymerization

Olefin copolymerization was conducted by the same method as Example 1, except that 5 µmol of the metallocene compound of the Preparation Example 2 was used.

Example 3

Solution Polymerization

Olefin copolymerization was conducted by the same method as Example 1, except that 5 µmol of the metallocene compound of the Preparation Example 3 was used.

Example 4

Supported Catalyst Polymerization 30 mg of the supported catalyst prepared in the Preparation Example 4 was quantified in a dry box and put in a 50 mL glass bottle, and then, the bottle was sealed with a rubber septum, and taken out of the dry box to prepare a catalyst to be introduced. Polymerization was conducted in a 2 L metal alloy reactor that is equipped with a mechanical stirrer, can be temperature-controlled, and is used at high pressure.

Into the reactor, 1.2 L of hexane containing 1.0 mmol of triethylaluminum was introduced, the above prepared supported catalyst was introduced without air contact, and then, polymerization was conducted for 1 hour while continuously adding gas ethylene monomers under pressure of 40 bar at 80° C. Stirring was discontinued, and then, ethylene was vented to remove, thus completing the polymerization. After filtering the polymerization solvent to remove most of them, the obtained polymer was dried in a vacuum oven of 80° C. for 12 hours.

Example 5

Supported Catalyst Polymerization

Copolymerization of ethylene-1-hexene was conducted by the same method as Example 4, except that the metallocene compound catalyst of Preparation Example 5 was used, and the obtained polymer was analyzed.

Example 6

Supported Catalyst Polymerization

Copolymerization of ethylene-1-hexene was conducted by the same method as Example 4, except that the metallocene compound catalyst of Preparation Example 6 was used, and the obtained polymer was analyzed.

Comparative Example 1

Solution Polymerization

Olefin copolymerization was conducted by the same method as Example 1, except that 5 μmol of the metallocene compound of Preparation Comparative Example 1 was used.

Comparative Example 2

Solution Polymerization

Olefin copolymerization was conducted by the same method as Example 1, except that 5 μmol of the metallocene compound of Preparation Comparative Example 2 was used.

Comparative Example 3

Supported Catalyst Polymerization

Olefin copolymerization was conducted by the same method as Example 4, except that 5 μmol of the metallocene compound of Preparation Comparative Example 1 was used.

Comparative Example 4

Supported Catalyst Polymerization

Olefin copolymerization was conducted by the same method as Example 4, except that 5 μmol of the metallocene compound of Preparation Comparative Example 2 was used.

Experimental Example (1) The catalytic activities of Examples 1 to 6 and Comparative Examples 1 to 4 were calculated by the ratio of the weight of produced polymer per mass of catalyst used, and the ratio of the weight of produced polymer per metallocene compound content in the catalyst, based on unit hour (h).

(2) And, the weight average molecular weights and molecular weight distributions of Examples 1 to 6 and Comparative Examples 1 to 4 were measured using high temperature GPC, and the results are shown in the following Table 1.

(2) The contents of 1-hexene in ethylene-1-hexene copolymers prepared in Examples 1 to 6 and Comparative Examples 1 to 4 were measured using 1H NMR, and the results are shown in the following Table 1.

TABLE 1

| | Catalyst used | 1-Hx content (mol %) | Activity (ton/ mol · hr) | Mw (g/mol) | PDI |
|---|---|---|---|---|---|
| Example 1 | Preparation Example 1 | 6.6 | 4.5 | 107,000 | 2.7 |
| Example 2 | Preparation Example 2 | 7.0 | 4.1 | 122,000 | 2.4 |
| Example 3 | Preparation Example 3 | 6.4 | 4.6 | 111,000 | 2.6 |
| Example 4 | Preparation Example 4 | 1.5 | 2.1 | 866,000 | 3.8 |
| Example 5 | Preparation Example 5 | 1.7 | 1.8 | 938,000 | 3.4 |

TABLE 1-continued

| | Catalyst used | 1-Hx content (mol %) | Activity (ton/ mol · hr) | Mw (g/mol) | PDI |
|---|---|---|---|---|---|
| Example 6 | Preparation Example 6 | 1.4 | 2.2 | 893,000 | 3.7 |
| Comparative Example 1 | Preparation Comparative Example 1 | 4.7 | 3.3 | 109,000 | 2.8 |
| Comparative Example 2 | Preparation Comparative Example 2 | 6.1 | 3.8 | 120,000 | 2.5 |
| Comparative Example 3 | Preparation Comparative Example 3 | 1.0 | 1.2 | 410,000 | 3.4 |
| Comparative Example 4 | Preparation Comparative Example 4 | 1.3 | 1.4 | 928,000 | 3.3 |

As shown in Table 1, the metallocene compounds of preparation examples and the catalyst compositions comprising the same exhibit high activity in copolymerization using comonomers, and yet, may improve comonomer insertion capability, and thus, may prepare an polyolefin-based copolymer that has high molecular weight as well as high 1-hexene content.

The invention claimed is:

1. A metallocene compound represented by the following Chemical Formula 2:

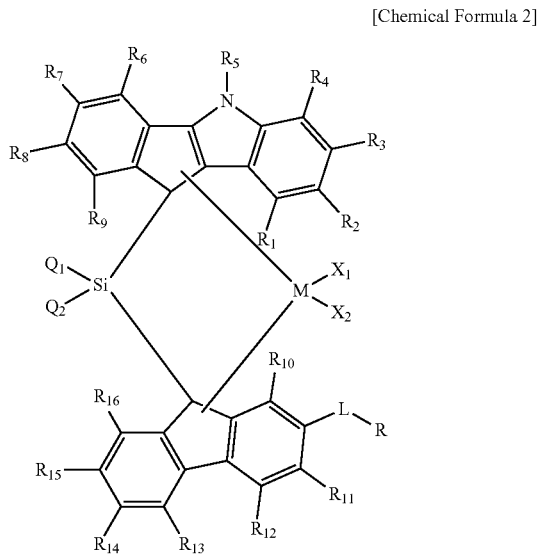

[Chemical Formula 2]

in the Chemical Formula 2,

M is a Group 4 transition metal;

$X_1$ and $X_2$ are identical or different, and are independently, halogen, a C1-20 alkyl group, a C2-20 alkenyl group, a C6-20 aryl group, a nitro group, an amido group, a C1-20 alkylsilyl group, a C1-20 alkoxy group, or a C1-20 sulfonate group;

$R_1$ to $R_{16}$ are identical or different, and are independently, hydrogen, halogen, a C1-20 alkyl group, a C2-20 alkenyl group, a C3-20 cycloalkyl group, a C4-20 cycloalkylalkyl group, a C1-20 alkoxy group, a C6-20 aryl group, a C5-20 heteroaryl group, a C7-20 alkylaryl group, or a C7-20 arylalkyl group, and two or more neighboring groups of $R_1$ to $R_{16}$ may be connected with each other to form a substituted or unsubstituted aliphatic or aromatic ring, provided that all of $R_1$ to $R_{16}$ are not hydrogen;

L is a direct bond or a C1-10 alkylene group;

R is a substituted or unsubstituted phenyl group, naphthyl group, C3-20 cycloalkyl group, or C1-20 alkoxyl group; and $Q_1$ and $Q_2$ are identical or different, and are independently, hydrogen, halogen, a C1-20 alkyl group, a C2-20 alkenyl group, a C1-20 alkoxy group, a C6-20 aryl group, a C7-20 alkylaryl group, or a C7-20 arylalkyl group.

2. The metallocene compound according to claim 1, wherein R in the Chemical Formula 2 is a phenyl group, a cyclopentyl group, a cyclohexyl group, a fluorophenyl group, or a pentafluorophenyl group.

3. The metallocene compound according to claim 1, wherein $R_2$ and $R_5$ in the Chemical Formula 2 are identical or different, and are independently, hydrogen or a C1-5 alkyl group.

4. The metallocene compound according to claim 1, wherein the compound represented by the Chemical Formula 2 has one of the following structural formulae:

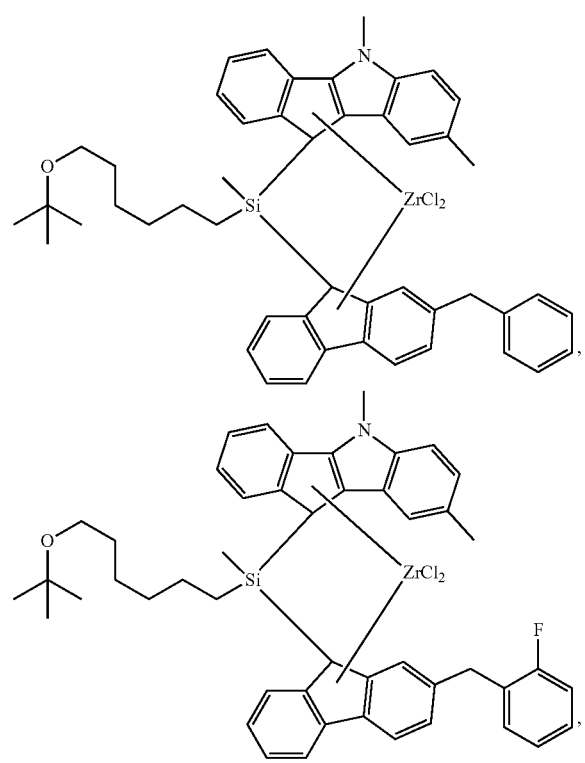

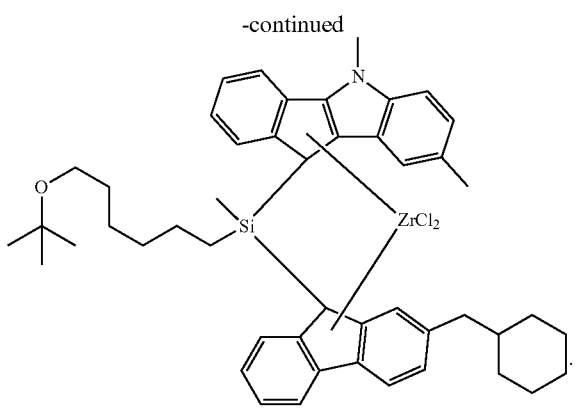

5. A method for preparing an olefin-based polymer, comprising a step of polymerizing olefin-based monomers in the presence of a catalyst composition comprising the metallocene compound of claim 1.

6. The method according to claim 5, wherein the catalyst composition comprises at least one cocatalyst compound selected from the group consisting of a compound represented by the following Chemical Formula 3, a compound represented by the following Chemical Formula 4, and a compound represented by the following Chemical Formula 5:

—[Al($R_{17}$)—O]n-    [Chemical Formula 3]

in the Chemical Formula 3, $R_{17}$ is a halogen radical, a C1-20 hydrocarbyl radical, a C1-20 hydrocarbyl radical substituted with halogen, and n is an integer of 2 or more, D($R_{18}$)$_3$    [Chemical Formula 4]

in the Chemical Formula 4,

D is aluminum or boron, and $R_{18}$ is C1-20 hydrocarbyl radical, or C1-20 hydrocarbyl radical substituted with halogen,

[L-H]$^+$[ZE$_4$]$^-$ or [L]$^+$[ZE$_4$]$^-$    [Chemical Formula 5]

in the Chemical Formula 5,

L is neutral or cationic Lewis base, H is a hydrogen atom, Z is a Group 13 atom, and Es are identical or different, and are independently a C6-20 aryl group or a C1-20 alkyl group, where one or more hydrogen atoms are unsubstituted or substituted with halogen, a hydrocarbon having a carbon number of 1 to 20, alkoxy or phenoxy.

7. The method according to claim 5, wherein the polymerization is conducted by a solution polymerization process, a slurry process or a gas phase process.

8. The method according to claim 5, wherein the olefin-based monomer is at least one selected from the group consisting of ethylene, propylene, 1-butene, 1-pentene, 4-methyl-l-pentene, 1-hexene, 1-heptene, 1-octene, 1-decene, 1-undecene, 1-dodecene, 1-tetradecene, 1-hexadecene, and 1-eicosene.

* * * * *